(12) United States Patent
Fletcher (10) Patent No.: US 7,325,837 B2
(45) Date of Patent: Feb. 5, 2008

(54) SELF LAMINATING SPECIMEN CAPTURE AND CONTAINMENT ASSEMBLY AND RECORDATION FORM COMBINATION

(75) Inventor: Donna J. Fletcher, Fort Scott, KS (US)

(73) Assignee: Ward Kraft, Inc., Fort Scott, KS (US)

( * ) Notice: Subject to any disclaimer, the term of this patent is extended or adjusted under 35 U.S.C. 154(b) by 781 days.

(21) Appl. No.: 10/899,230

(22) Filed: Jul. 26, 2004

(65) Prior Publication Data
US 2006/0020226 A1 Jan. 26, 2006

(51) Int. Cl.
*B42D 15/00* (2006.01)
(52) U.S. Cl. .................. 283/105; 283/74; 283/900; 462/1; 462/8; 206/569
(58) Field of Classification Search .............. 283/900, 283/81, 78, 68, 116, 74, 61, 105, 101, 107, 283/109; 462/1, 6, 7, 8, 28, 84, 22, 64, 903; 206/569, 570, 460, 776; 235/375, 380; 281/2, 281/5; 428/43, 192, 201, 204; 604/317, 604/318; 422/55, 56, 102; 435/309.1
See application file for complete search history.

(56) References Cited

U.S. PATENT DOCUMENTS

| | | | | | |
|---|---|---|---|---|---|
| 3,843,452 | A | * | 10/1974 | Freake et al. | 435/287.8 |
| 4,055,394 | A | * | 10/1977 | Friedman et al. | 422/56 |
| 4,259,964 | A | * | 4/1981 | Levine | 600/371 |
| 4,706,996 | A | * | 11/1987 | Fasham | 462/55 |
| 5,114,188 | A | * | 5/1992 | Koch | 283/68 |
| 5,190,049 | A | * | 3/1993 | Briggs et al. | 600/573 |
| 5,223,405 | A | * | 6/1993 | Howell et al. | 435/30 |
| 5,582,298 | A | * | 12/1996 | Clayton et al. | 206/569 |
| 5,948,687 | A | * | 9/1999 | Cleator | 436/66 |
| 6,016,345 | A | * | 1/2000 | Quattrocchi | 379/265.02 |
| 6,152,493 | A | * | 11/2000 | Draper | 283/74 |
| 6,260,885 | B1 | * | 7/2001 | Massimo, Sr. | 283/68 |
| 6,474,694 | B1 | * | 11/2002 | Emmert et al. | 283/56 |
| 6,599,481 | B2 | * | 7/2003 | Stevens et al. | 422/102 |
| 6,607,699 | B1 | * | 8/2003 | Elliott et al. | 422/61 |
| 6,713,142 | B1 | * | 3/2004 | Arway et al. | 428/40.1 |
| 2004/0160054 | A1 | * | 8/2004 | Davin | 283/74 |

* cited by examiner

*Primary Examiner*—Monica Carter
*Assistant Examiner*—Jamila Williams
(74) *Attorney, Agent, or Firm*—Michael C. Maier (57) ABSTRACT

The present invention is a specimen capture and collection form that utilizes a self laminating form assembly having first and second separable parts one of which is used in the collection, capture and retention of a sample of material to be analyzed and the other of which is used for recording the particular transaction for which the sample of specimen was collected. The form assembly is also provided with a unique element which enables the separation of excess sample collection material to be easily and conveniently separated from the remainder of the form assembly so as to not contaminate the specimen as well as prevent the inadvertent removal of the specimen from the form assembly. The construction is also provided with distinct verification areas to confirm authenticity of the form construction.

21 Claims, 5 Drawing Sheets

SELF LAMINATING SPECIMEN CAPTURE AND CONTAINMENT ASSEMBLY AND RECORDATION FORM COMBINATION

CROSS-REFERENCES TO RELATED APPLICATIONS

None.

FIELD OF THE INVENTION

The present invention relates to a self laminating specimen capture assembly that includes a combination business form and specimen collection assembly that is suitable for collecting and transmitting samples for analysis. The business form construction of the present invention includes a specimen collection portion and an information recordation portion as well as one or more separable form segments that are used to retain information relating to the sample or specimen that has been collected. In addition, the form assembly includes a unique means for conveniently separating unused collection material from that portion of the material holding or containing the specimen. The business form construction also includes the use of one or more identification or verification sections that serve to verify the source from which the sample or specimen was obtained. The form assembly is suitable for use in a number of applications in which it may be necessary to collect evidentiary materials for use in criminal investigations, paternity, and the like, confirming pedigree in veterinarian fields, disease tolerance in plants and agricultural applications and source analysis in connection with livestock studies as well as disease treatment and prevention.

BACKGROUND OF THE INVENTION

There are various needs in the fields of law enforcement or investigative services, site preservation, medical, agricultural and other applications in which it is often necessary to collect samples or specimens for testing, verification, contagious disease containment, legal applications, and any other endeavor that may require the collection, preservation and transmission of a sample or specimen, in a suitable assembly, from one location to another.

With respect to the field of law enforcement or investigative services, an officer, detective or other investigator, such as a private investigator, forensic scientist and the like may be required to collect specimens, samples, materials, and other evidence at the scene of an event, such as a crime, in order to preserve and protect any critical or important evidence that may be used in solving the crime or explaining the event that has occurred and lead to the investigator being present. Such samples are typically used for DNA (deoxyribonucleic acid) analysis to connect a possible defendant to the crime or event. Maintaining the integrity of such samples is absolutely critical in attempting to obtain conviction of the possible defendant.

Historic preservation and archeological expeditions also may require the collection and safe-keeping of samples of material that are collected from the site, structure or location of the collection effort. For example, in the restoration of a historic building, many layers of paint may have accumulated over the years and stripping away and collecting a sample from each layer may be important in analyzing and verifying the age of the structure. In addition, such paint samples may be necessary in matching the particular or original color the structure was painted so that the restoration when completed is authentic.

Archeological expeditions require painstaking removal of debris and dirt that has amassed over a site of interest over a period of time ranging from several decades to centuries to millennia. Each layer contains invaluable information about the history of the site and may require carbon dating, chemical evaluation and other analysis to be conducted during each period of time being studied to better understand the age and speed of deterioration of the site so that additional steps may be undertaken to preserve the site. In addition, human and animal remains, when discovered also need to be collected and transmitted in a manner so that the location can be verified and the integrity of the sample maintained so that there is no confusion about the age of the site or the inhabitants that may have occupied the site at one time.

The medical field regularly collects samples and specimens of biological material such as tissue, blood, saliva, seamen and other bodily fluids and matching the integrity of the sample to the patient or donor in order to ensure the adequate and proper treatment of the patient submitting the samples or from whom the samples were procured from. In addition, sample collection and preservation is also very important in areas where contagious diseases have broken out so that proper analysis can be conducted and treatment arranged for the relevant portion of the population.

The legal profession also requires a means by which to collect and preserve information, samples, specimens and other evidence for client's files or in investigating certain events. In addition, sample collection from crime scenes for criminal defendants is also important. Other uses may include collections of samples and specimen for the purposes of evaluating products, processes and materials from competitors and the like.

Agriculture scientists and veterinarians also periodically require the collection of samples and specimens for research and study. Exemplary uses may include blood samples for determination of pedigree of a particular line of animals. Testing for disease in animals such as "mad cow" disease also requires the period testing of biological samples in an effort to determine whether a herd has been infected with a disease. Collecting plant tissue can also aid in research, breeding of crops and testing for disease or resistance to certain herbicides.

Each of the foregoing applications and many others not enumerated above, such as use in horticulture and collecting herbarium samples, etc. require the ability to collect, retain, transmit and verify the integrity and chain of custody during each phase of the handling of the sample, specimen, etc.

Presently, there are a number of products available in the marketplace for certain uses. These may range from single bags with resealable, mechanical closures (hook and loop, rib and channel, etc.) with a place for indicia to be printed on the bag to more elaborate sample collection bags that may have a reusable opening to enable access to the sample and then a single re-closing of the container until the sample finally reaches its destination. Still other products include a sample collection bag that may have a record receiving ply connected to the bag so that a record can accompany the bag and a receipt attached at the place of origin to prove continuing custody of the sample or specimen unit.

Another product offering includes a bag with plural seals to open and subsequently close and secure the sample and then a plurality of labels that enable placement of a label on a specimen collector as well as on a record receipt for the purposes of record retention by the investigator or other person enclosing the sample or specimen.

While the products are generally effective for the uses that these constructions have been put to, they still however suffer from various drawbacks. Often these sample collection units are constructed of a single ply or may be made from a transparent material so that the sample may be damaged by ultraviolet degradation, or may simply be removed by someone that does not want the sample to reach its final destination.

In order to attempt to defeat this situation, such sample bags have been placed in separate boxes, bags and the like however, such a process requires that the sample collector locate such an auxiliary structure. In addition, such auxiliary structures, if the source is unknown or if care of the structure has not been continuously monitored, the structure can contaminate the sample or material contained within the bag. Alternatively, if the sample collected is for DNA analysis, the outer structure may contaminate the sample bag depending on the sealing nature of the outer structure or any pathogens that may be present at the location the auxiliary structure was manufactured, located or handled.

In addition, these prior art constructions require the sample or specimen to often be placed into and removed from the collection bag several times for testing and analysis which can lead to possible contamination of the sample and potentially lead to distorting the results of the analysis performed on the sample or specimen.

What is needed therefor is a sample, specimen, material collection device that lends some universality to the collection needs of various industries and applications for which specimen collection is required and which provides a composite construction that overcomes the foregoing difficulties while meeting the needs and applications for such a diverse arrangement of needs and requirements.

BRIEF SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

The present invention is directed to a novel form construction that is used in the collection and containment of samples or specimens that have been collected for the purposes of research, evaluation, testing and analysis. The form construction includes a self laminating portion which can be used to securely affix a material containing a specimen securely within the form assembly. The construction includes first and second portions, the first portion is used as the specimen or sample collection portion and the second portion is used as the information recordation portion and has one or more separable record plies. The form assembly includes one or more finger or thumb print panels that are used for verification of the source from which the sample is collected. The form assembly includes the use of a serrated edge so that excess sample collection material can be removed so as to prevent the inadvertent removal of the sample from the assembly.

In one exemplary embodiment of the present invention, a specimen capture and collection form assembly is provided and includes a substrate that has first and second portions. The substrate has first and second transversely extending sides and first and second longitudinally extending ends and a top face and a bottom face. The first and second portions of the substrate are separable from one another by a line of weakness, and the first portion has a first area and the second portion has a second area that is distinct from the first area. Each of the first and second portions of the substrate also have verification panels.

Continuing with a description of the presently described embodiment, a pattern of adhesive is applied to the top face of the first portion of the substrate. A containment ply is applied over the pattern of adhesive and is connected to the first portion. The containment ply has a die cut window therein. The containment ply with the adhesive and the first portion forming a specimen capture and collection portion. At least one removable recordation ply is affixed to the second portion of the substrate. The removable recordation ply along with the second portion creates an information capture section.

The presently described embodiment also includes material tear off assist that is provided on the specimen capture and collection portion of the assembly and is used to separate a sample collection portion from an unused material portion of a sample collection device.

In a further exemplary embodiment of the present invention, method of using a specimen collection form assembly, is provided and includes the steps of initially providing at least one specimen collection form. The form has a substrate that is divided into first and second portions. The first portion includes a pattern of adhesive and has a containment ply that is disposed over the pattern of adhesive, with at least one of the containment ply and the first portion having a die cut window therein. The second portion of the form assembly has at least one recordation ply that is disposed over the second portion and each of the first and second portions has a verification panel.

Next, and according to the exemplary method that is described a specimen collection material is obtained and then the specimen is collected on the material. The material with the specimen is then positioned on the pattern of adhesive on the first portion of the substrate. Finally, the containment ply is sealed over the material with the specimen such that at least a portion of the specimen is visible through the die cut window provided in the construction.

Once the specimen has been collected, excess collection material may be removed through the use of a serrated edge that is provided on the first portion. Information about the sample or the source of the sample is collected on the recordation form and finger or thumb prints can be obtained from the donor of the sample or the investigator collecting the sample. The sample or specimen may then be analyzed through at least one die cut window that is provided in the form construction.

In a yet still further embodiment of the present invention, a specimen collection kit, is described and includes a series of collection forms. Each of the form includes a substrate that has first and second portions. The substrate has first and second transversely extending sides and first and second longitudinally extending ends and a top face and a bottom face. The first and second portions are separable from one another by a line of weakness, and the first portion has a first area and the second portion has a second area that is distinct from the first area, and each of the first and second portions has verification panel.

In the presently described kit embodiment, a pattern of adhesive is applied to the top face of the first portion of the substrate. A containment ply is also supplied and is applied over the pattern of adhesive and is connected to the first portion by the adhesive. The containment ply has a die cut window therein. The containment ply with the adhesive and the first portion form a specimen capture and collection portion of the form assembly.

Still continuing with the forms included in the kit assembly of the present invention, at least one removable recordation ply is affixed to the second portion of the substrate. The removable recordation ply with the second portion creating an information capture section. A material tear off is provided on the specimen capture and collection portion of the assembly and is used to separate a sample collection portion from an unused material portion of a sample collection device.

The kit of the present embodiment also includes a collection material and a package that is sized and configured to hold the series of forms and the collection material. The package may also include finger print kits, and may be over wrapped to provide security for the package.

In a yet still further embodiment of the present invention, a self laminating form assembly for mounting a specimen for analysis is described and includes a panel that is divided into separable first and second portions by a line of weakness. The first portion of the panel includes a pattern of adhesive, and has a cover ply that is provided over the pattern of adhesive. A release liner is provided over the adhesive and is removed to expose the adhesive. The cover ply is substantially coextensive with the first portion and at least one die cut window is provided in one of the cover ply and first portion of the panel. A serrated edge is provided on one of the first portion of the panel and the cover ply for severing excess collection material.

In the presently described embodiment, the second portion of the panel has at least one recordation ply that is affixed to the second portion. The recordation ply is capable of receiving information relating to a specimen to be collected. A collection material that contains a specimen is secured to at least a portion of the pattern of the adhesive and between the first portion and the cover ply. A finger or thumb print panel is provided on each of the first and second portions of the panel.

These and other objects of the invention will become clear from an inspection of the detailed description of the invention and from the appended claims.

BRIEF DESCRIPTION OF THE DRAWING

These, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

The present invention is now illustrated in greater detail by way of the following detailed description which represents the best presently known mode of carrying out the invention. However, it should be understood that this description is not to be used to limit the present invention, but rather, is provided for the purpose of illustrating the general features of the invention.

The present invention provides a unique form construction that is suitable for use in collecting specimens and samples and includes a self laminating configuration portion that adequately secures the sample and collection material directly to the form assembly. The form construction is suitable for use in a number of applications including legal, medical, criminal, investigative and other areas where it is useful or desirable to collect materials to aid in the evaluation, testing or research and has a recordation portion to archive or record the transaction that lead to the collection of the sample.

Figure 1:
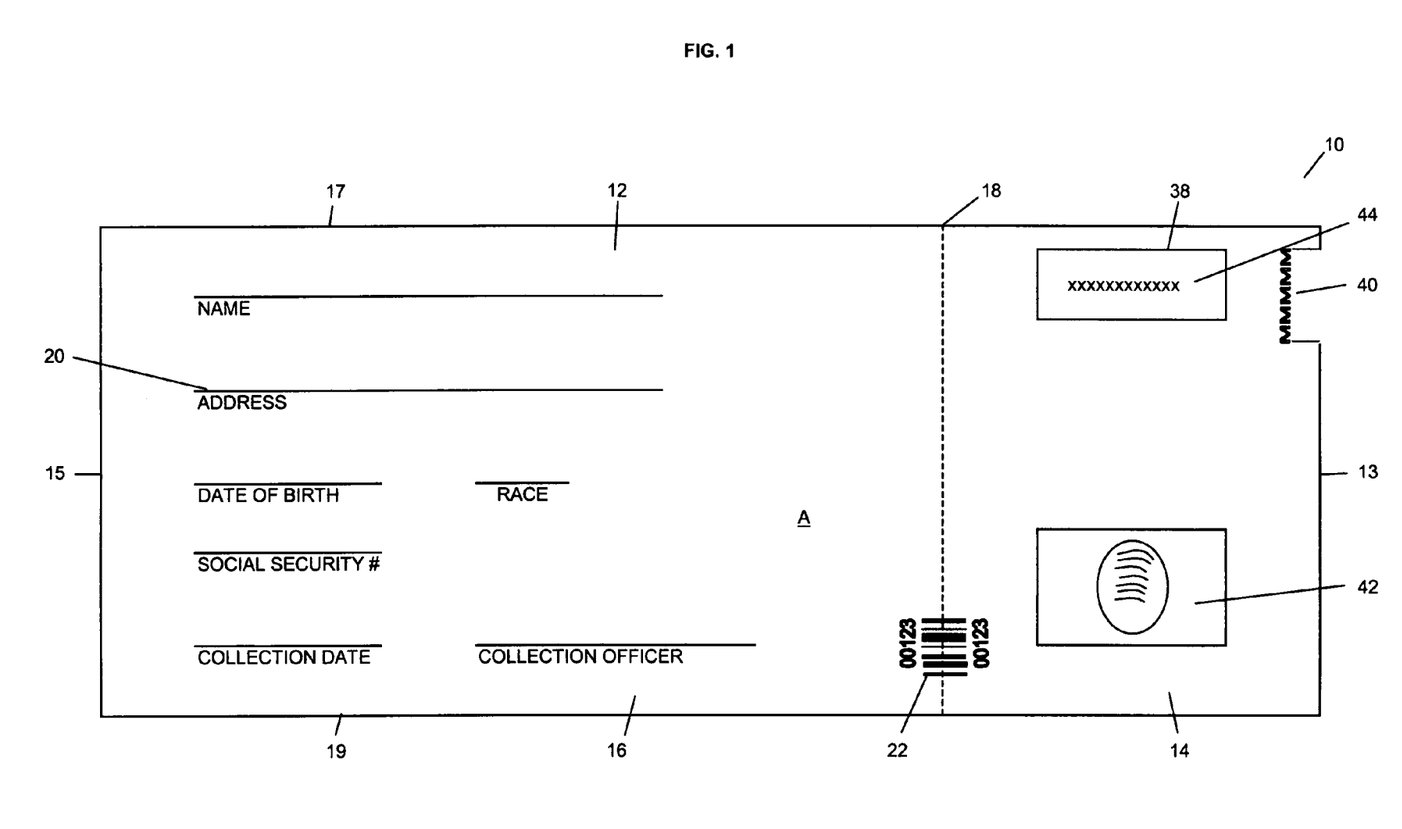
FIG. 1 depicts a front view of the form construction of the present invention.

Turning now to FIG. 1 of the presently described embodiment, the form assembly is generally depicted by reference to numeral 10. The form assembly 10 includes a substrate or panel 12 that is divided into first and second portions 14 and 16. The portions are separable from one another along a line of weakness 18. The line of weakness will generally be a line of perforations that consist of a series of cuts and ties to separate the portions 14 and 16 from one another. As can be seen from the FIGURE, second portion 16 has an area and the first portion has an area, each of which are distinct from one another. The area of the first portion 14 is smaller than the area of the second portion 16. It should be understood that the areas could be substantially equivalent or the area of the first portion (the collection portion) 14 may represent between 25% and 33% of the area of the second area or recordation portion 16.

The substrate or panel 12 is preferably constructed from a cellulosic based material such as card or tag stock ranging in the 60 to 100 pound range, but may consist of other suitable material that is sufficient for providing support to the form configuration and processing the form for analysis.

Figure 3:
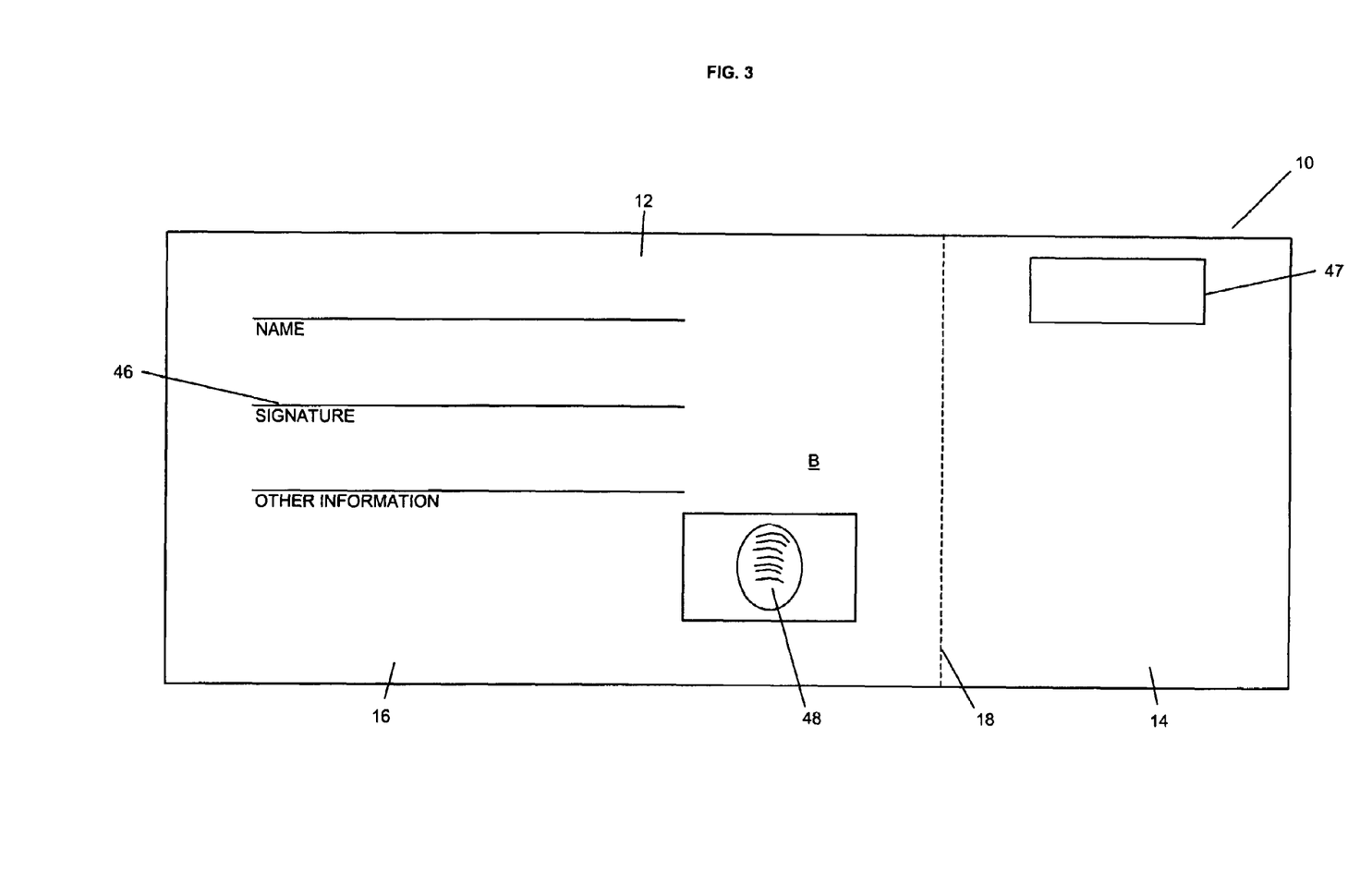
FIG. 3 illustrates a back view of the form construction of the present invention.

The substrate or panel 12 has first and second longitudinally extending ends 13 and 15 and first and second transversely extending sides 17 and 19 and top and bottom faces "A" and "B" (shown in FIG. 3).

The first portion 14 along with other components to be described herein will become the self-laminating specimen holding portion of the form. The second portion 16 along with one or more record plies will be the portion of the form that is used in the recording of information. The second portion 16 is provided with a number of areas 20 for which relevant collection indicia can be provided. Such indicia may include but is not limited to name, address, date of birth, social security numbers, collection information and any other information that might be pertinent to the particular collection.

The top face of the form assembly 10 is also provided with a bar code 22 which is disposed over the line of weakness 18 so that each portion of the form 14 and 16 will contain a portion of the bar coding so as to be able to confirm the tracking and tracing of the information that is associated with the collected sample.

Figure 2:
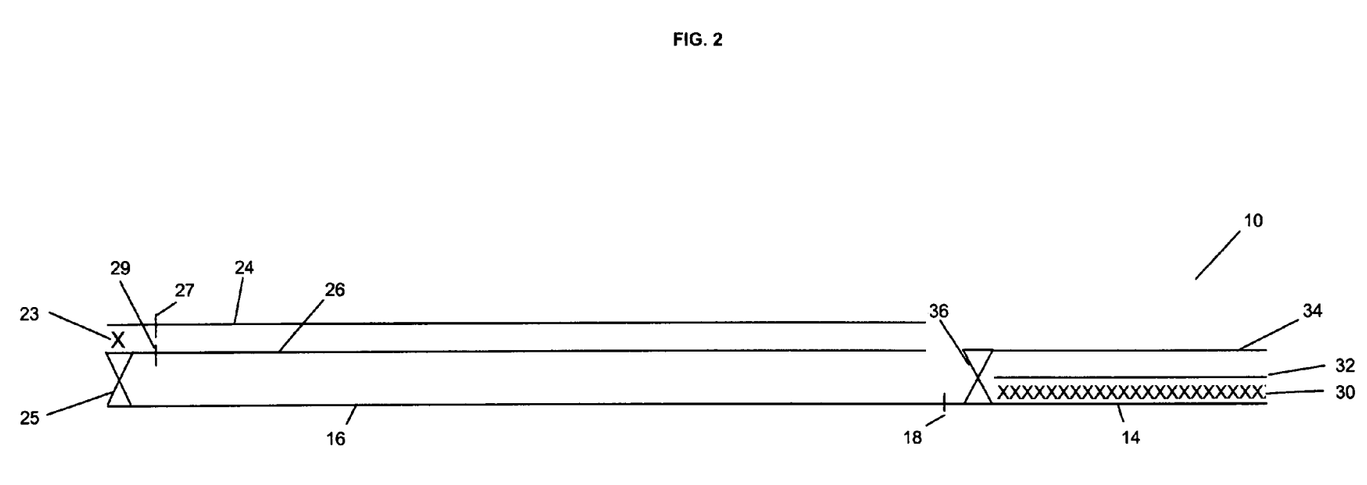
FIG. 2 provides a side view of the form construction of the present invention showing the plies of the assembly.

Turning to FIG. 2, a cross sectional view of the form assembly is provided and includes the substrate or panel 12 having the first and second portions 14 and 16 and line of weakness 18. On the second portion 16 of the form construction a pair of recordation plies 24 and 26 are provided. The plies 24 and 26 are connected to the second portion 16 of the substrate 12 by lines of adhesive 23 and 25. The plies 24 and 26 are separable from the form assembly 10 through use of lines of weakness 27 and 29. As shown, the plies 24 and 26 are substantially coextensive with the second portion 16 of the substrate 12. However, it should be understood that one ply may be longer than the other or the plies may be shorter (in width and length) of the second portion 16 of the substrate 12 depending on the needs of the investigator or collector. While the plies 24 and 26 are shown on top of the substrate 12, it should be understood that the plies may also appear on the back of the substrate 12 and that the FIGURE is used only for exemplary illustration.

The recordation plies may be provided with carbonless coatings (not shown) such as CF (coated front) and CB (coated back) which will enable an imprint, such as from a stylus (pen, pencil, etc.) that is applied to the top or upper most ply 24 to transfer to any underlying ply 26 including the base substrate 12.

The first portion 14 of the assembly 10 includes a pattern of adhesive 30 which is covered by a release liner 32. The adhesive 30 is preferably a permanent adhesive such as an acrylic or rubber based adhesive. The release liner is a silicone coated material that will readily release from the adhesive upon applying sufficient peeling strength.

Over the top of the release liner 32 and adhesive 30 is a containment ply 34. The ply is a paper based ply, which may include tag or card stock. The containment ply 34 is connected to the first portion 14 of the substrate 12 by a line of adhesive 36.

As can be seen in FIG. 1, the containment ply 34 is shown over the first portion 14 and includes a die cut window 38, serrated cut out 40 which is used in cooperation with a twisting motion to assist in the trimming or ripping of excess collection material and finger print patch or verification panel 42. The serrated cut out 40 is also used to indicate the correct side for with the collection material 44 should be drawn out and torn from the assembly. The die cut out 38 is sized and configured such that the sample when placed on the collection material 44 is visible through the window 38 such that a sampling apparatus (not shown) can enter the window and remove a portion of the sample material for testing and analysis. The serrated cut out 40 is spaced from and parallel to the die cut out 40 and is adjacent the end edge of the containment ply.

The collection material is a relatively absorbent material such as gauze, spun cotton material, synthetic wicking material and the like. The material once the sample or specimen has been collected is placed on the adhesive pattern 30 and then pulled up against the serrated edge 40 so that the collection material may be torn off so that no excess material is left hanging out of the form that could become inadvertently caught causing the sample to become dislodged from the containment portion of the form assembly 10.

Turning now to FIG. 3 of the present specification, the back face or bottom "B" of the form assembly 10 is shown. Portions 14 and 16 of the substrate or panel 12 are again visible and separable from one another along line of weakness 18.

The back face "B" of the substrate 12 is also provided with areas 46 for capturing the indicia that is relevant to the investigation or collection. Such areas may include signature segments, names and other information that may be suitable or relevant for collecting and retaining information. In addition, verification panel 48 is also provided and as shown in the present FIGURE panel 48 is a finger or thumb print panel. In this way, the verification panel 42 as shown in FIG. 1 can be used to match the finger print panel 48 in FIG. 3 such that the information and sample collected can be verified and the authenticity confirmed. It should be understood that instead of finger print panels other independent verification means could be used such as labels, receipts, tags, RFID tags, encoded chips and the like so that the integrity of the sample and record can be maintained.

In addition, the substrate 12 is provided with a die cut out window 47 in the first portion 14. The die cut window 47 and the window 38 (shown in FIG. 1) would preferably be provided in alignment with one another such that the sample or specimen could be cut out from either side of the first portion 14.

Figure 4:
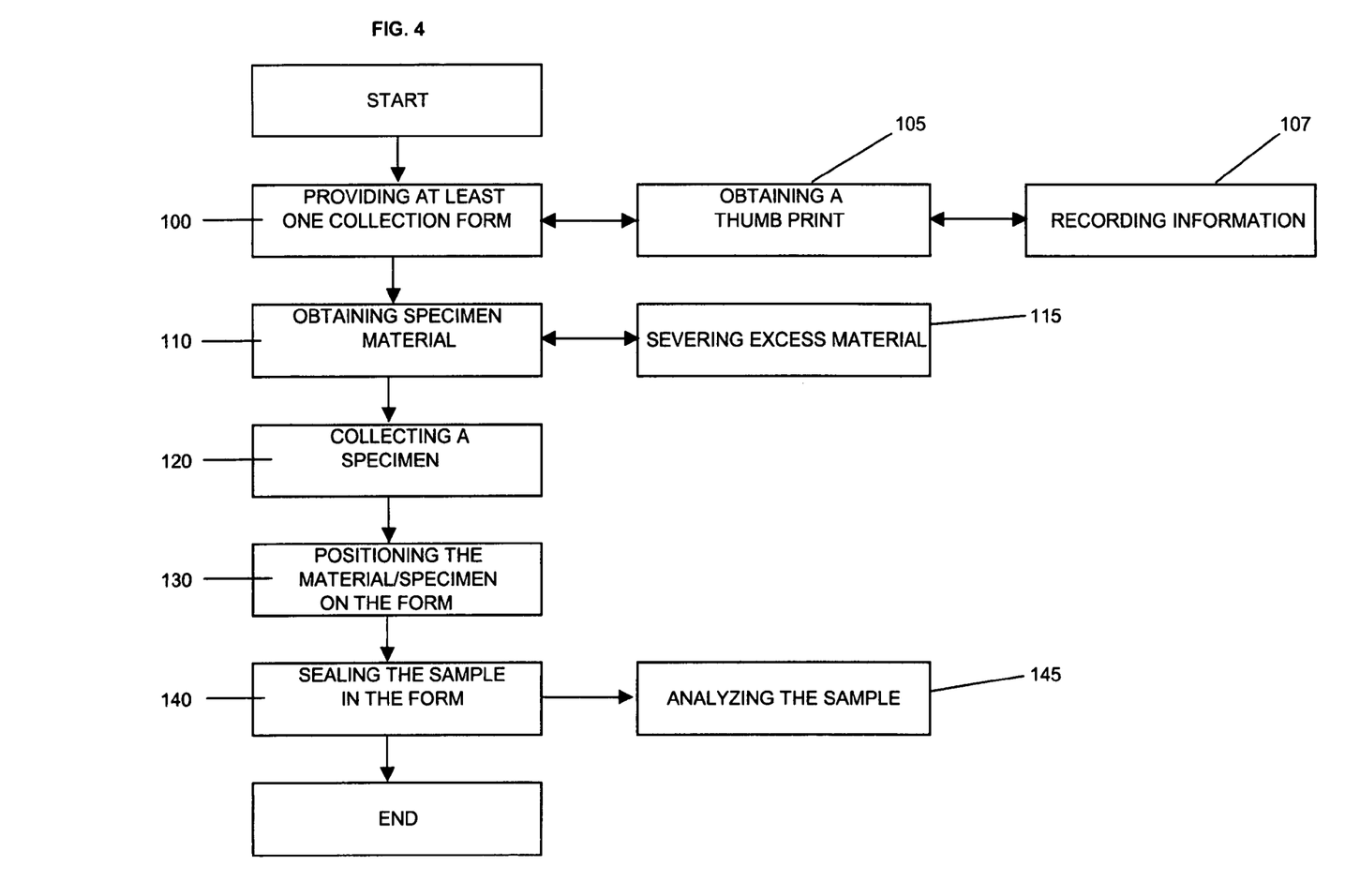
FIG. 4 presents a block diagram showing an exemplary method of using the present invention.

Reference is now directed to FIG. 4 of the present invention in which an exemplary method of using the form assembly is provided. Once the process has been started, at least one form assembly, having the construction previously described and illustrated in the foregoing description and drawings is provided at step 100. The user of the form assembly may proceed to collect a thumb or finnger print from the individual from which the specimen or sample is to be collected at step 105. The sample or specimen that is to be collected can be biological such as bodily fluids, hair and nail samples and the like. In addition, if the sample to be collected is at a particular location the sample or specimen could be a chemical or other substance.

In addition to preparing the form assembly for use, the recordation portion of the form assembly may be completed at step 107. The recordation portion may include the insertion of information such as name, address, description of the individual, social security number, date of birth, etc. and such other information that may be useful in preserving the specimen.

Next, a suitable sample collection material is obtained at step 110. The sample collection material, if the sample is a biological fluid, may be selected from a group of absorbent materials. Alternatively, if the sample is some other sort of specimen, the collection material selected would be one that does not interfere with or contaminate the sample. Once the type of specimen or sample has been identified, the specimen or sample is collected at step 120. The specimen or sample is applied to the collection material in various methods that are known and will not be described herein.

Once the sample has been collected as described above, the sample is positioned on the pattern of adhesive on the first portion of the form construction at step 130. The adhesive will securely anchor the specimen containing material to the form assembly and the material with the sample should be arranged or position such that the sample is visible through the die cut window.

The sample and collection material are then sealed in the form at step 140. Sealing occurs through the use of the pattern of adhesive and pressing the containment ply over the top of the sample and collection material. This self-laminating construction will desirably hold the sample and collection material in place while the form is transported for purposes of analysis, evaluation and research which may be done at step 145. After the sealing of the containment ply over the top of the sample and collection material, any excess collection material may be removed through the use of the serrated edge discussed above that is positioned adjacent the edge of the die cut window. Once the form has been received for analysis, the exemplary method for the present discussion ends. There may of course be further steps such as retaining the form sections for record or file purposes and matching the portions of the form together after they were initially separated from one another.

Alternatively, where a collector is used the assembly may be sent along with the collector to the lab and a laboratory or analysis point will then place a portion of the collected material with the assembly.

Figure 5:
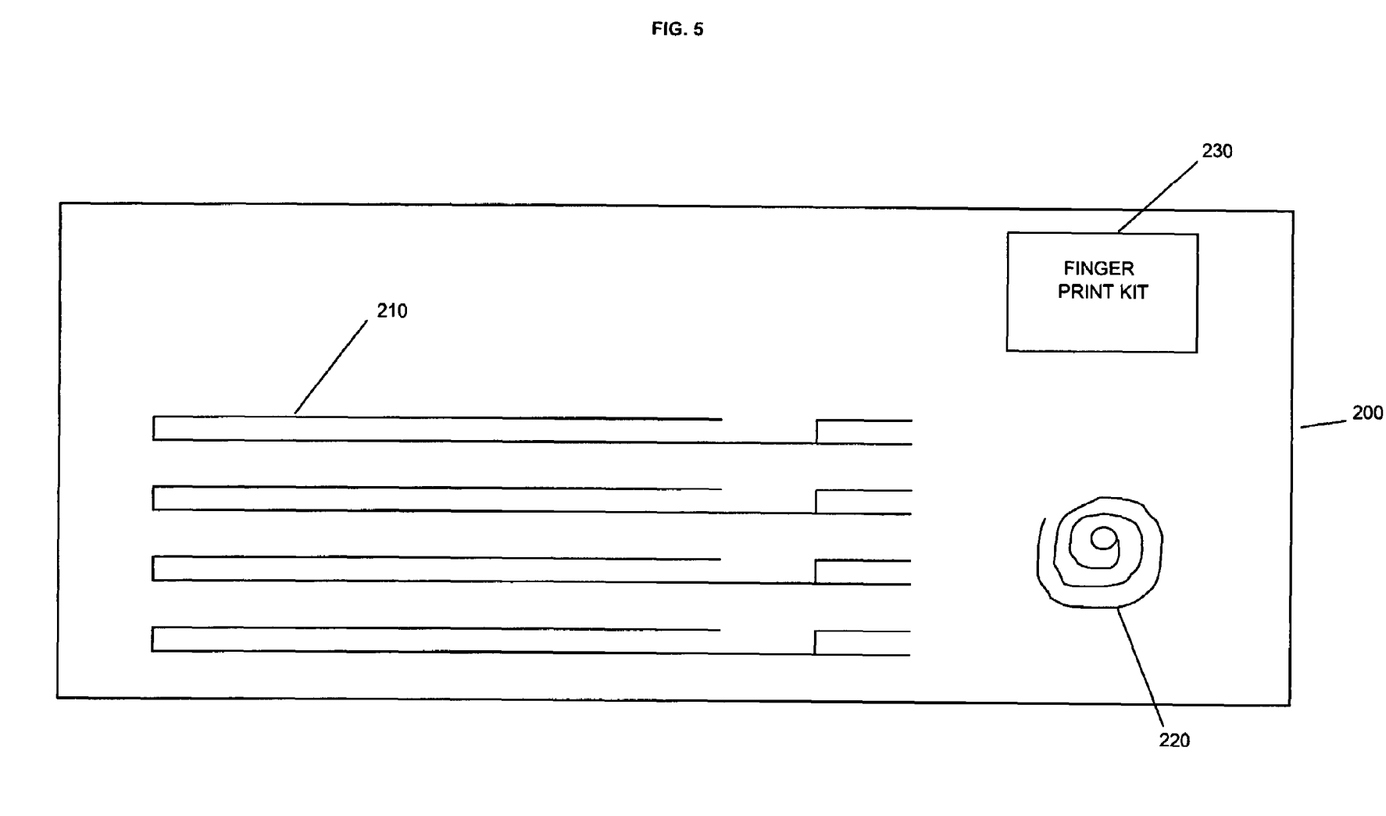
FIG. 5 shows a kit utilizing the form assemblies of the present invention.

Reference is now directed to FIG. 5, in which a kit is depicted that utilizes a series of form assemblies that are constructed in accordance with the description provided herein. A package 200 is provided. The package may include a box, envelope, tote, carton, pouch or other container that is suitable for transport. The package 200 includes a series of form assemblies 210. In addition, the package 200 is also provided with a supply of collection material 220 as previously described herein. The package 200 may further include a finger print kit 230 and such other items or elements that are necessary in order to complete the package or kit such as a writing or impact stylus, instructions and the like. The package may also be over wrapped with plastic or protective film so as to maintain the integrity of the contents.

It will thus be seen according to the present invention a highly advantageous specimen containment and collection form assembly has been provided. While the invention has been described in connection with what is presently considered to be the most practical and preferred embodiment, it will be apparent to those of ordinary skill in the art that the invention is not to be limited to the disclosed embodiment, that many modifications and equivalent arrangements may be made thereof within the scope of the invention, which scope is to be accorded the broadest interpretation of the appended claims so as to encompass all equivalent structures and products.

The inventors hereby state their intent to rely on the Doctrine of Equivalents to determine and assess the reasonably fair scope of their invention as it pertains to any apparatus, system, method or article not materially departing from but outside the literal scope of the invention as set out in the following claims.

The invention claimed is:

1. A specimen capture and collection form assembly, comprising;
    a substrate having first and second portions, said substrate having first and second transversely extending sides and first and second longitudinally extending ends and a top face and a bottom face;
    said first and second portions separable from one another by a line of weakness, and said first portion having a first area and said second portion having a second area distinct from said first area, and each of said first and second portions having verification panel;
    a pattern of adhesive is applied to said top face of said first portion of said substrate;
    a containment ply is applied over said pattern of adhesive and is connected to said first portion, said containment ply having a die cut window therein, said containment ply with said adhesive and said first portion forming a specimen capture and collection portion;
    at least one removable recordation ply affixed to said second portion of said substrate, said removable recordation ply with said second portion creating an information capture section; and
    a material tear off assist is provided on said specimen capture and collection portion to separate a sample collection portion from an unused material portion of a sample collection device.

2. A specimen capture and collection form assembly as recited in claim 1, wherein each of said verification panels on said first and second portions is for collecting at least one finger or thumb print.

3. A specimen capture and collection form assembly as recited in claim 1, wherein a bar code is provided over said line of weakness.

4. A specimen capture and collection form assembly as recited in claim 1, wherein a release liner is provided over said pattern of adhesive.

5. A specimen capture and collection form assembly as recited in claim 1, wherein said material tear off assist is a serrated edge.

6. A specimen capture and collection form assembly as recited in claim 1, wherein said first portion is provided with a die cut window.

7. A specimen capture and collection form assembly as recited in claim 6, wherein said die cut window in said first portion is in alignment with said die cut window in said containment ply.

8. A specimen capture and collection form assembly as recited in claim 1, wherein said containment ply is substantially coextensive with said first portion of said substrate.

9. A specimen capture and collection form assembly as recited in claim 1, wherein said at least one recordation ply is substantially coextensive with said second portion of said substrate.

10. A specimen capture and collection form assembly as recited in claim 1, wherein plural recordation plies are provided on said second portion of said substrate.

11. A method of using a specimen collection form assembly, comprising the steps of;
    providing at least one specimen collection form, said form having a substrate divided into first and second portions, said first portion including a pattern of adhesive and a containment ply disposed over said pattern of adhesive, with at least one of said containment ply and said first portion having a die cut window therein; said second portion having at least one recordation ply disposed thereover and each of said first and second portions having a verification panel;
    obtaining a specimen collection material;
    collecting said specimen on said material;
    positioning said material with said specimen on said pattern of adhesive on said first portion of said substrate;
    sealing said containment ply over said material with said specimen such that at least a portion of said specimen is visible through said die cut window.

12. A method as recited in claim 11, including a further step of severing excess specimen collection material prior to the step of sealing said containment ply over said material with said specimen.

13. A method as recited in claim 11, including a further step of analyzing said specimen through said at least one die cut window after the step of sealing said containment ply over said material with said specimen.

14. A method as recited in claim 11, including a further step of obtaining a finger or thumb print at any time after the step of providing the specimen collection form.

15. A method as recited in claim 11, including a further step of recording information on said recordation ply at any time after the step of providing the specimen collection form.

16. A method as recited in claim 12, wherein said excess material is severed through use of a serrated edge provided on one of said containment ply and said first portion of said substrate.

17. A specimen collection kit, comprising;
    a series of collection forms, each of said form including a substrate having first and second portions, said substrate having first and second transversely extending sides and first and second longitudinally extending ends and a top face and a bottom face;

said first and second portions separable from one another by a line of weakness, and said first portion having a first area and said second portion having a second area distinct from said first area, and each of said first and second portions having verification panel;

a pattern of adhesive is applied to said top face of said first portion of said substrate;

a containment ply is applied over said pattern of adhesive and is connected to said first portion by said adhesive, said containment ply having a die cut window therein, said containment ply with said adhesive and said first portion forming a specimen capture and collection portion;

at least one removable recordation ply affixed to said second portion of said substrate, said removable recordation ply with said second portion creating an information capture section;

a material tear off is provided on said specimen capture and collection portion to separate a sample collection portion from an unused material portion of a sample collection device;

a collection material; and a package sized and configured to hold said series of forms and said collection material.

18. A specimen collection kit as recited in claim 17, wherein said package includes a fingerprint kit.

19. A specimen collection kit as recited in claim 17, wherein said package includes instructions on using said forms and said collection material.

20. A specimen collection kit as recited in claim 17, wherein said package is wrapped for protection.

21. A self laminating form assembly for mounting a specimen for analysis, comprising;

a panel divided into separable first and second portions, with said portions divided by a line of weakness, said first portion including a pattern of adhesive, and cover ply provided over said pattern of adhesive and release liner, said cover ply being substantially coextensive with said first portion, at least one die cut window provided in one of said cover ply and first portion of said panel, and a serrated edge provided on one of said first portion of said panel and said cover ply for severing excess collection material;

said second portion having at least one recordation ply affixed thereto, said recordation ply capable of receiving information relating to a specimen to be collected;

a collection material containing a specimen secured to at least a portion of said pattern of said adhesive and between said first portion and said cover ply; and a finger or thumb print panel provided on each of said first and second portions of said panel.

* * * * *